(12) United States Patent
Chee

(10) Patent No.: US 7,879,600 B2
(45) Date of Patent: Feb. 1, 2011

(54) WASTE CONVERTER

(76) Inventor: Eng Lock David Chee, 12 Abrolhos Loop, Beckenham, WA 6107 (AU)

( * ) Notice: Subject to any disclaimer, the term of this patent is extended or adjusted under 35 U.S.C. 154(b) by 439 days.

(21) Appl. No.: 11/913,449

(22) PCT Filed: May 5, 2006

(86) PCT No.: PCT/IB2006/001493

§ 371 (c)(1), (2), (4) Date: Nov. 2, 2007

(87) PCT Pub. No.: WO2006/120569

PCT Pub. Date: Nov. 16, 2006

(65) Prior Publication Data

US 2008/0206856 A1    Aug. 28, 2008

(30) Foreign Application Priority Data

May 6, 2005    (AU) ............................. 2005902290

(51) Int. Cl.
*C12M 1/02*    (2006.01)
*C05F 9/02*    (2006.01)

(52) U.S. Cl. ................................ 435/290.2; 435/290.4

(58) Field of Classification Search ... 435/290.1–290.4; C05F 9/02, 9/06, 11/06
See application file for complete search history.

(56) References Cited

U.S. PATENT DOCUMENTS

| | | | | |
|---|---|---|---|---|
| 4,984,561 A * | 1/1991 | Warrington | ............... | 435/290.1 |
| 5,545,559 A * | 8/1996 | Kariniemi | ................ | 435/290.1 |
| 5,589,391 A * | 12/1996 | Fink | ......................... | 435/290.3 |
| 5,894,780 A * | 4/1999 | Taniguchi | ......................... | 71/9 |
| 5,994,122 A * | 11/1999 | Cooper et al. | ............. | 435/290.1 |
| 6,837,393 B1 * | 1/2005 | Kuo | ........................... | 220/263 |
| 2001/0009771 A1 * | 7/2001 | West | ....................... | 435/290.1 |
| 2004/0076475 A1 * | 4/2004 | Bell | ..................... | 405/129.45 |

FOREIGN PATENT DOCUMENTS

| | | |
|---|---|---|
| AU | 200114981 B2 | 3/2005 |
| EP | 0 210 382 A1 * | 6/1986 |
| WO | 0220428 A1 | 3/2002 |
| WO | WO 03/086489 A1 * | 10/2003 |

OTHER PUBLICATIONS

Derwent Abstract Accession No. 94-015435/02, TW 215070 A, Mitsui Kinzoku Staff Service KK, Oct. 21, 1993.

* cited by examiner

*Primary Examiner*—William H Beisner
*Assistant Examiner*—Michael Hobbs
(74) *Attorney, Agent, or Firm*—Brooks Kushman P.C.

(57) ABSTRACT

A waste converter (10) for domestic use includes two waste conversion regions. Household waste is placed in a primary waste conversion region (40) which includes flies and maggots. When waste has sufficiently decomposed it falls through to a secondary waste conversion region which includes composting worms and woodlice.

22 Claims, 3 Drawing Sheets

WASTE CONVERTER

FIELD OF THE INVENTION

The present invention relates to a converter for biodegradable household waste such as kitchen waste.

BACKGROUND TO THE INVENTION

It is known to use worm farms for converting vegetable scraps into organic matter for use in gardens. Domestic worm farms typically have: side walls including air vents to allow for the circulation of air within the worm farm and side doors to allow the removal of worm castings; a lid which is removable to allow for the placement of new vegetable matter on top of the existing matter; a sump in which liquid can collect; and a drain to allow removal of collected liquid in the sump. Known domestic worm farms are created from moulded plastics such as PVC.

There are several problems which have been identified with the use of domestic worm farms to convert household waste. One such problem is the propensity for flies and other insects to breed in the worm farm. The flies can enter and leave the worm farm through the air vents, and also when the lid is opened as new material is added.

Another limitation with known domestic worm farms is the limitation in types of materials which may be put into the worm farm. Kitchen waste products such as meat and acidic fruits cannot be used in known worm farms, as meat rots with a malodorous result and acidic conditions are detrimental to composting worms. The presence of rotting meat contaminates the worm castings liquid drained from the worm farm, and also encourages the breeding of flies.

A further limitation of known domestic worm farms is that matter added to a worm farm must be cut into small pieces prior to addition.

The present invention attempts to overcome at least in part some of the aforementioned disadvantages of previous worm farms.

SUMMARY OF THE INVENTION

In accordance with one aspect of the present invention there is provided a waste converter having a waste deposit aperture in which waste can be received, the waste converter having a primary waste conversion region and a secondary waste conversion region, wherein the waste deposit aperture allows the introduction of waste matter such as kitchen scraps into the primary waste conversion region, the primary waste conversion region being defined by a outer skin having a plurality of apertures contained therein to permit the passage of partially composted waste from the primary waste conversion region to the secondary waste conversion region, the primary waste conversion region including, in use, insects which assist to decompose meat, and the secondary waste conversion region including composting worms. Preferably, the secondary waste conversion region includes woodlice.

BRIEF DESCRIPTION OF THE DRAWINGS

The present invention will now be described, by way of example, with reference to the accompanying drawings, in which.

DESCRIPTION OF PREFERRED EMBODIMENTS

Figure 1:
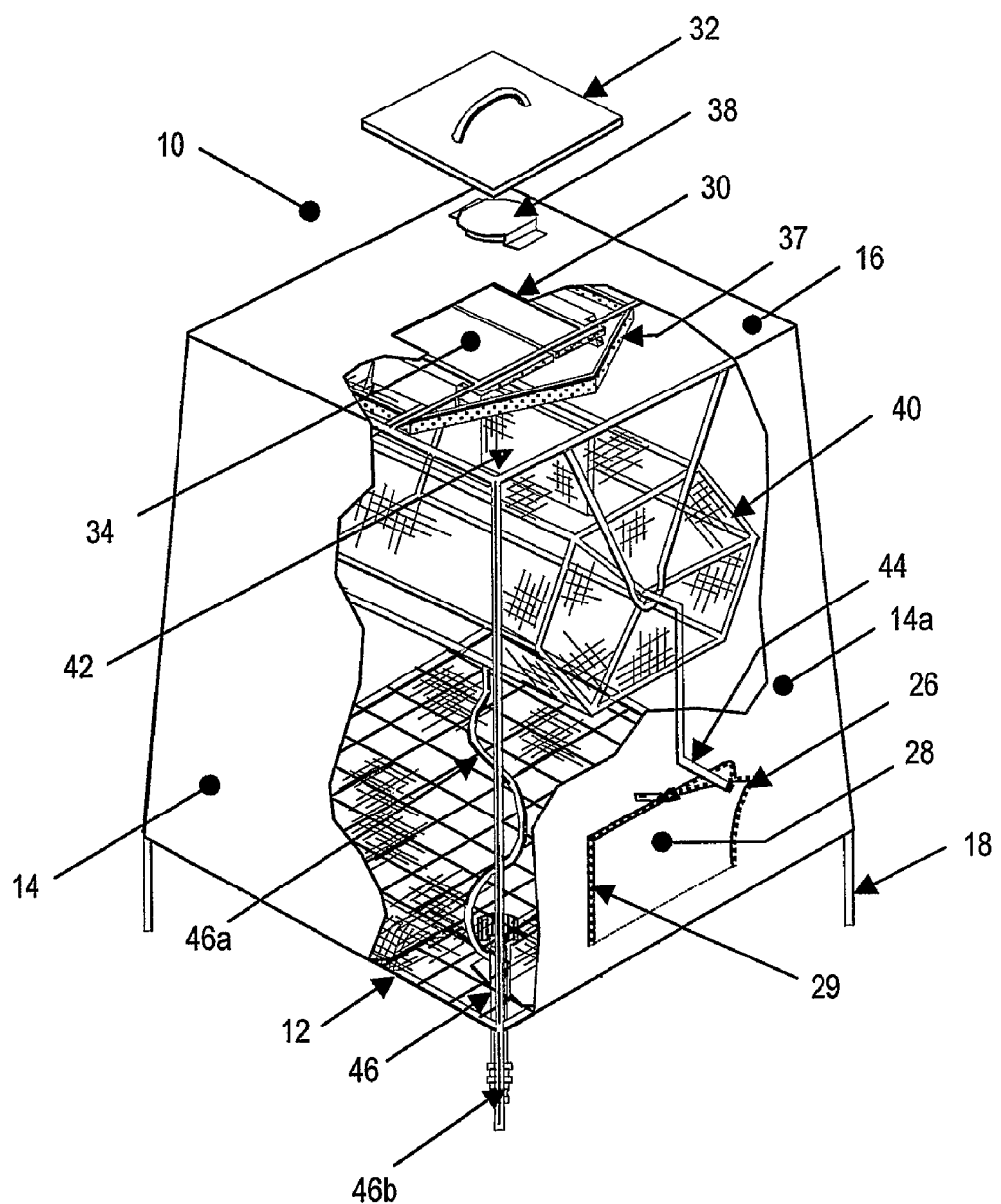
FIG. 1 is a cutaway view of a waste converter in accordance with a first embodiment of the present invention.

Referring to the Figures, there is shown a waste converter 10. The waste converter 10 comprises a substantially square base 12, four substantially trapezoidal side walls 14 and a substantially square top enclosing portion 16. The waste converter 10 is tapered upwardly such that the top enclosing portion 16 is smaller than the base 12. The base 12 is supported at corners thereof by legs 18.

Figure 2:
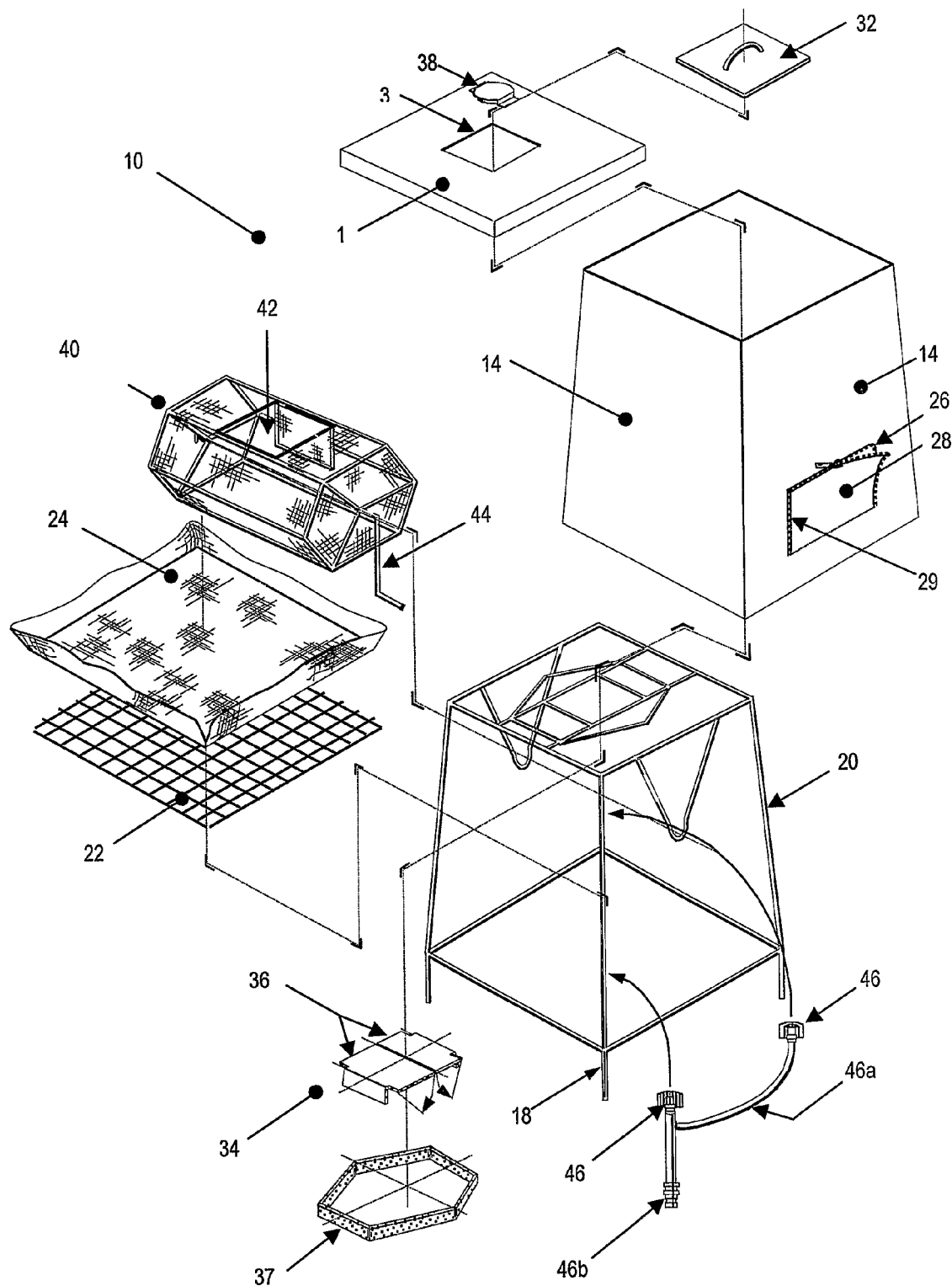
FIG. 2 is an exploded view of the waste converter of FIG. 1.

A preferred construction of the waste converter 10 is shown in FIG. 2. In this embodiment, the waste converter 10 has a frame 20 constructed of suitably rigid, strong, corrosion resistant material such as galvanised steel. In a preferred embodiment of the invention the frame is constructed from 10 mm galvanised steel rod for the legs 18 and for supporting the base 12, and from 6 mm galvanised steel rod for supporting the side walls 14 and the top enclosing portion 16.

The base 12 is water permeable. Preferably, the base 12 comprises a substantially square wire mesh 22 which is mounted by suitable means such as welding to the frame 20. The wire mesh 22 is typically comprised of 1.24 mm galvanised wire with 50 mm spacing. An insect screen 24 is fixed by suitable means to the wire mesh 22. The insect screen 24 is preferably comprised of 0.25 mm diameter fibreglass screening material. The insect screen 24 may comprise several diagonally offset layers of standard insect screening material, or may alternatively comprise a single layer of "microscreen" material.

The side walls 14 are comprised of flexible, light-resistant material such as black polyethylene plastic. Preferably, the light-resistant material is not susceptible to degradation by exposure to UV radiation. At least one side wall 14a includes an access portion 26. The access portion 26 has a covering flap 28 composed of the same material as the side walls 14. The covering flap 28 is fastened to the side wall 14a by suitable means such as a zipper 29.

The top enclosing portion 16 has a centrally located waste deposit aperture 30 covered, in use, by a cover 32.

A gate 34 is located directly beneath the waste deposit aperture 30. The gate 34 comprises a pair of shutters 36 which are biased in a closed position, but able to open downwardly into the waste converter 10. The shutters 36 thus allow for the ingress of material into the waste converter 10, but prevent the egress of flies and other insects. The gate 34 is surrounded by a barrier 37 which extends downwardly from the top enclosing portion 16. The barrier 37 has an outer face directed towards the side walls 14. The outer face is comprised of a maggot-retarding material. In a preferred embodiment of the invention, the outer face is comprised of a fibrous nylon material such as carpet, having a fibre length of about 8-10 mm.

It is anticipated that maggots encountering the barrier 37 are unlikely to progress through it, being more likely to nest within the fibres. It will be appreciated that maggots beyond a certain size will be unable to pass around the lower end of the barrier 37.

The top enclosing portion also has a fly trap 38 located in a corner thereof. The flytrap 38 is arranged to permit the ingress of flies into the waste converter 10, but prevent their egress.

The interior of the waste converter 10 is divided into two regions, a primary waste conversion region and a secondary waste conversion region. The primary waste conversion region is defined by a hexagonal-prism shaped tumbler 40. The tumbler 40 occupies approximately the upper two thirds of the waste converter 10.

The tumbler 40 is formed from a skin including a plurality of apertures. In a preferred embodiment of the invention, the skin is formed from a wire mesh material having apertures approximately 10 mm across.

The tumbler 40 includes a waste acceptance receptacle 42 in an upper surface thereof. The waste acceptance receptacle 42 is covered by an internally opening door, which swings open when at the top of the tumbler 40 and swings closed when in other positions. The waste acceptance receptacle 42 when at the top of the tumbler is located directly beneath the gate 34, and is thus able to receive waste placed in the waste deposit aperture 30.

The tumbler 40 further includes a handle 44 which extends through a side wall 14 of the waste converter 10, to enable agitation and spinning of the tumbler 40.

The secondary waste conversion region is located above the base 12 of the waste converter 10.

In use, waste such as kitchen waste is supplied through the waste deposit aperture 30, the gate 34 and the waste acceptance receptacle 42 into the primary waste conversion region. Within the primary waste conversion region an ecological system including bacteria and insects such as flies and maggots exists. The organisms within the primary waste conversion region act on the waste to at least partially decompose the waste. This process may be exothermic, and may operate at a relatively high temperature of up to 40° C.

The handle 44 can be used to agitate the tumbler 40 and thus arrange for even distribution of decomposing waste, in addition to assisting aerobic conversion. The internal door of the waste acceptance receptacle 42 prevents large pieces of undecomposed waste falling from the primary to the secondary waste conversion region. In the event that the primary waste conversion region is overfilled, the internal door will be prevented from closing and thus a small amount of waste may fall from the primary waste conversion region to the secondary waste conversion region upon rotation of the tumbler 40.

When waste has decomposed sufficiently to fall through the apertures in the skin of the tumbler 40, this waste falls into the secondary waste conversion region. The secondary waste conversion includes composting worms, woodlice and other suitable insects such as flies. Waste in this region composts relatively quickly when compared to the primary waste conversion region.

Preferably, water jets 46 at the side or corners of the waste converter 10 supply sprays of water into the waste converter 10 to assist the decomposition process. The water jets 46 are connected to an external water supply via a hose 46a and water connection socket 46b.

Air is able to enter the waste converter through the base 12, the waste deposit aperture 30 and the fly trap 38.

Figure 3:
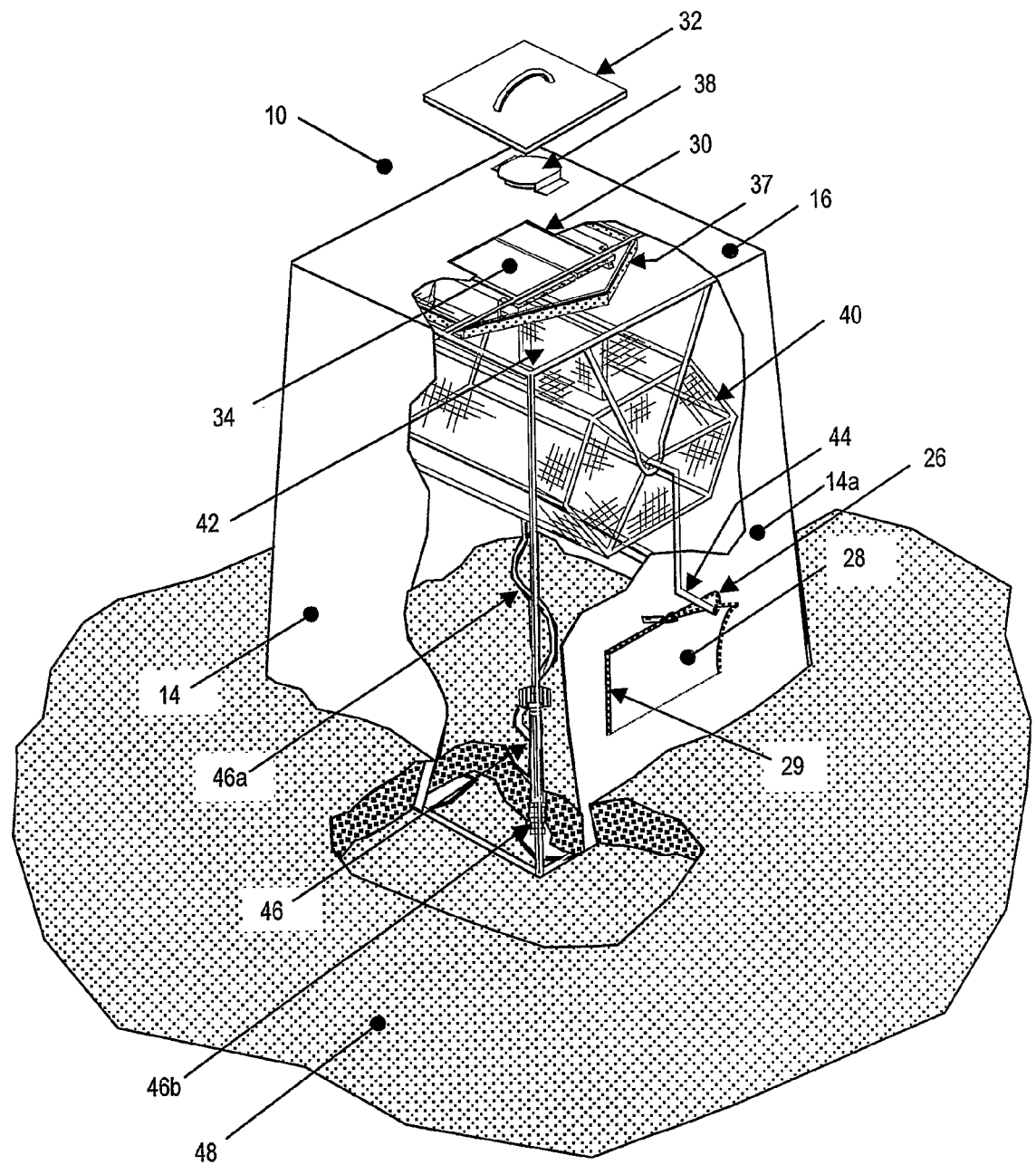
FIG. 3 is a cutaway view of a waste converter in accordance with a second embodiment of the present invention.

A second embodiment of the invention is shown in FIG. 3. In the embodiment of FIG. 3 the waste converter 10 is inserted within soil 48. In this embodiment, the base 12 is no longer required. The composting worms and other insects lie within the soil 48. Other than this difference, the waste converter 10 of this embodiment functions in the same way as that of the first embodiment.

Modifications and variations as would be apparent to a skilled addressee are deemed to be within the scope of the present invention.

The invention claimed is:

1. A waste converter for decomposing biodegradable waste, the waste converter comprising:
    an enclosure having a top enclosing portion, a peripheral side wall and an open bottom defining an internal cavity, the top enclosing portion having a cover and a waste deposit aperture for introducing waste into the waste converter;
    a primary waste conversion region located within the enclosure, the primary waste conversion region being defined by a tumbler formed from an outer skin having a plurality of apertures wherein the tumbler includes a waste acceptance receptacle located, in use, beneath the waste deposit aperture; and
    a secondary waste conversion region located within the enclosure, below the primary waste conversion region and above a water permeable base, the water permeable base being supported by legs above the ground, wherein the plurality of apertures of the tumbler allow partially composted waste to pass from the primary waste conversion region to the secondary waste conversion region to further decompose.

2. A waste converter as claimed in claim 1, wherein the apertures are approximately 10 mm across.

3. A waste converter as claimed in claim 1, wherein the tumbler can be agitated and spun.

4. A waste converter as claimed in claim 3, wherein the tumbler includes a handle which extends through a side wall of the waste converter to enable agitation and spinning of the tumbler.

5. A waste converter as claimed in claim 1, wherein the waste acceptance receptacle being covered by a door, the door being arranged such that it swings to a closed position when not at the top of the tumbler.

6. A waste converter as claimed in claim 5, wherein the door opens internally of the tumbler.

7. A waste converter as claimed in claim 1, wherein the tumbler is hexagonal-prism shaped.

8. A waste converter as claimed in claim 1, wherein the primary waste conversion region is above the secondary waste conversion region.

9. A waste converter as claimed in claim 8, wherein the primary waste conversion region occupies about the upper two-thirds of the waste converter.

10. A waste converter as claimed in claim 1, wherein the secondary waste conversion region includes woodlice.

11. A waste converter as claimed in claim 1, wherein the waste converter is formed from a flexible, light-resistant material mounted on a rigid frame.

12. A waste converter as claimed in claim 11, wherein the flexible material is polyethylene plastic.

13. A waste converter as claimed in claim 11, wherein the frame is formed from galvanized steel rod.

14. A waste converter as claimed in claim 1, wherein the waste converter has a side wall including an access portion.

15. A waste converter as claimed in claim 14, wherein the access portion has a covering flap fastened by a zipper.

16. A waste converter as claimed in claim 1, wherein the waste converter includes a gate located directly beneath the waste deposit aperture, the gate being biased towards a closed position.

17. A waste converter as claimed in claim 16, wherein the gate comprises a pair of shutters able to open downwardly into the waste converter.

18. A waste converter as claimed in claim 1, wherein the waste deposit aperture is surrounded by a barrier, the barrier having an outer face comprised of a maggot-retarding material.

19. A waste converter as claimed in claim 18, wherein the maggot-retarding material is fibrous.

20. A waste converter as claimed in claim 1, wherein the waste converter includes a fly trap arranged to permit the ingress of flies into the waste converter and to prevent their egress.

21. A waste converter as claimed in claim 1, wherein the waste converter has a substantially square base comprised of water permeable material.

22. A waste converter as claimed in claim 21, wherein the water permeable material is screen material.

* * * * *